(12) United States Patent
Kuebler

(10) Patent No.: US 11,630,294 B2
(45) Date of Patent: Apr. 18, 2023

(54) SURGICAL MICROSCOPE HAVING AN ILLUMINATION APPARATUS

(71) Applicant: Carl Zeiss Meditec AG, Jena (DE)

(72) Inventor: Carl Kuebler, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 232 days.

(21) Appl. No.: 16/276,284

(22) Filed: Feb. 14, 2019

(65) Prior Publication Data

US 2019/0258043 A1    Aug. 22, 2019

(30) Foreign Application Priority Data

Feb. 16, 2018   (DE) .................... 10 2018 202 423.5
May 4, 2018    (DE) .................... 10 2018 110 806.0

(51) Int. Cl.
*G02B 21/06* (2006.01)
*G02B 21/00* (2006.01)
(Continued)

(52) U.S. Cl.
CPC .......... *G02B 21/06* (2013.01); *G02B 21/0012* (2013.01); *G02B 21/0092* (2013.01);
(Continued)

(58) Field of Classification Search
CPC ............... G02B 21/06; G02B 21/0092; G02B 21/0012; G02B 21/361; G02B 21/22; G02B 21/36; A61B 90/30; A61B 90/20
(Continued)

(56) References Cited

U.S. PATENT DOCUMENTS

| 6,587,711 | B1 | 7/2003 | Alfano et al. |
| 7,215,468 | B2 | 5/2007 | Nakata |

(Continued)

FOREIGN PATENT DOCUMENTS

| CN | 106707487 A | 5/2017 |
| DE | 10250953 A1 | 5/2004 |
| DE | 102014114013 A1 | 3/2016 |

OTHER PUBLICATIONS

Bashkatov et al.: "Optical properties of human stomach mucosa in the spectral range from 400 to 2000 nm: Prognosis for gastroenterology," Medical Laser Application 22, pp. 95-104, (2007).
(Continued)

*Primary Examiner* — George G. King
(74) *Attorney, Agent, or Firm* — Ewers IP Law PLLC; Falk Ewers

(57) ABSTRACT

A surgical microscope for visualizing a tissue region contains an illumination device with a light source and an illumination beam path for illuminating an object region with an object plane and an observation device having an observation beam path for imaging the object region with the object plane into an observation plane. A first polarizer can be coupled into the illumination beam path and is suitable for polarizing the illumination light in a first orientation. A polarizer, which can be coupled into the observation beam path, has a second orientation at an angle between 80° and 100° relative to the first orientation. In a first mode, the light source emits illumination light in a first wavelength range between 450 nm and 550 nm, the first polarizer is coupled into the illumination beam path, and the second polarizer is coupled into the observation beam path.

5 Claims, 6 Drawing Sheets

(51) Int. Cl.
  *A61B 90/20* (2016.01)
  *A61B 90/30* (2016.01)
  *G02B 21/22* (2006.01)
  *G02B 21/36* (2006.01)

(52) U.S. Cl.
  CPC .............. *A61B 90/20* (2016.02); *A61B 90/30* (2016.02); *G02B 21/22* (2013.01); *G02B 21/36* (2013.01); *G02B 21/361* (2013.01)

(58) Field of Classification Search
  USPC ........................................................ 359/386
  See application file for complete search history.

(56) References Cited

U.S. PATENT DOCUMENTS

| | | | |
|---|---|---|---|
| 2002/0109912 A1 | 8/2002 | Knoblich | |
| 2007/0211460 A1* | 9/2007 | Ravkin | G02B 6/0068 362/231 |
| 2008/0106787 A1 | 5/2008 | Tsutsui et al. | |
| 2008/0132794 A1 | 6/2008 | Alfano et al. | |
| 2010/0085637 A1* | 4/2010 | Liu | G02B 21/0092 359/386 |
| 2010/0277794 A1* | 11/2010 | Utsugi | G02B 21/0032 359/386 |
| 2010/0321773 A1* | 12/2010 | Chen | G02B 21/0032 359/386 |
| 2016/0091702 A1 | 3/2016 | Hauger | |
| 2016/0154229 A1* | 6/2016 | Milner | G06T 7/80 348/79 |
| 2018/0180865 A1 | 6/2018 | Ma et al. | |
| 2020/0026090 A1* | 1/2020 | Hargis | G02B 27/0927 |
| 2021/0294085 A1* | 9/2021 | Dowaki | G02B 21/365 |

OTHER PUBLICATIONS

Pentax Medical: "Pentax I-ScanTM Functionality, Application and Technical Anlysis " (MK-412 Rev: A) available at https://www.pentaxmedical.com/pentax/download/fstore/uploadFiles/Pdfs/Case%20Studies/AMER_GI_CS_MK-412-Rev.-A_i-SCAN-White-Paper%20(1)_3.pdf (last accessed Feb. 8, 2019)—Copyright 2013.

Olympus: "Narrow Band Imaging in ENT—Review of Clinical Evidence," published Jun. 2015.

S.L. Jaques et al.: "Polarized light imaging specifies the anisotropy of light scattering in the superfical layer of a tissue," J. Biomed. Opt. 21 (7) 071115 (2016).

GM Kamphuis et al.: "Storz Professional Image Enhancement System: A New Technique to Improve Endoscopic Bladder Imaging," J Cancer Sci Ther 8:3 (2016).

Office action by the German Patent and Trademark Office (DPMA) issued in German patent application 10 2018 110 803.0, which is a counterpart hereof, dated Oct. 5, 2018, and English-language translation thereof.

Office Action issued in German Patent Application No. DE 10 2018 110 806.0 dated Nov. 4, 2019 (from which this application claims priority) and English language translation thereof.

* cited by examiner

SURGICAL MICROSCOPE HAVING AN ILLUMINATION APPARATUS

CROSS REFERENCE TO RELATED APPLICATIONS

This application claims priority to German patent applications DE 10 2018 202 423.5, filed on Feb. 16, 2018, and DE 10 2018 110 806.0, filed on May 4, 2018, both of which are hereby incorporated by reference in their entireties.

TECHNICAL FIELD

The disclosure relates to a surgical microscope having an illumination apparatus with a light source for illuminating an object region with an object plane and an observation apparatus for imaging the object region with the object plane into an observation plane. The disclosure also relates to a method for visualizing the object region.

BACKGROUND

The object region can be formed by a tissue region, comprising mucous membrane, also referred to as mucosa. The mucous membrane is a protective layer lining the interior of hollow organs. One example of a tissue region comprising a mucous membrane is the larynx. By way of a tube inserted into the mouth and throat, a channel leading to the larynx region is formed, through which the tissue region can be observed using a surgical microscope. Further areas of application are the observation of the mucosa in the oral cavity and of the base of the tongue, the cervical mucosa, of the eardrum etc.

Mucosa regions can be well supplied with blood and be covered by a liquid film. The liquid film is strongly reflective, which means that observation using a surgical microscope can be impaired. During a surgery that is to be performed in such a region, it is important for the observer, who may be a surgeon, to be able to clearly see capillaries and blood vessels in the mucosa or in the underlying tissue to reliably avoid unintended injuries.

US 2002/0109912 A1 discloses the use of polarization means in a surgical microscope with coaxial illumination to reduce reflections in highly reflective surfaces. However, the use of polarization means to reduce reflections is rejected in US 2002/0109912 A1 due to the absorption by two polarization filters which accompanies the polarization and to the associated intensity decrease.

Moreover, DE 10 2014 114 013 A1 discloses a surgical microscope having a first settable polarizer in the illumination beam path and a second settable polarizer in the observation beam path, wherein the polarization direction of the polarizer in the illumination beam path is optimized with respect to the orientation of the nerve fiber tracts and the polarization direction of the polarizer in the observation beam path is optimized with respect to the rotation of the polarization direction by the nerve fibers. The system described in DE 10 2014 114 013 A1 is not used to reduce reflections in highly reflective surfaces.

It is also possible to use endoscopic imaging systems to observe capillaries and blood vessels in the upper mucosa and the underlying tissue. The endoscopes are equipped with a camera for this purpose. The images recorded by the camera are displayed on a display.

It is known from "PENTAX i-SCAN™ Functionality, Application and Technical Analysis" (MK-412 Rev: A) of PENTAX Medical from 2013 retrievable via the link www-.pentaxmedical.com/pentax/download/fstore/uploadFiles/Pdfs/Case %20Studies/AMER_GI_CS_MK-412-Rev.-A_i-SCAN-White-Paper %20(1)_3.pdf to apply digital post-treatment to images recorded with a digital endoscope to increase contrast.

The article "Narrow Band Imaging in ENT—Review of Clinical Evidence" (E0492289·2.000·06/15·PR·HB) by Olympus Europe SE & Co. KG retrievable via the link www.olympus-europa.com/medical/rmt/media/Content/Content-MSD/Documents/Clinical-Studies/E0492289_ENT-NBI_clinical_study_brochure_EN_20150630_final.pdf describes an endoscopy method in which a narrowband illumination in the green and blue spectral range is used for tumor detection and to increase contrast between capillaries in the mucosa and veins in the submucosa.

G M Kamphuis et al. "Storz Professional Image Enhancement System: A New Technique to Improve Endoscopic Bladder Imaging," J Cancer Sci Ther 2016 8:3 likewise describes an endoscopy method in which a narrowband illumination in the green and blue spectral range is used to increase contrast.

The images obtained with an endoscope, however, are not stereoscopic and therefore do not provide any three-dimensional image information to the observer, who may be a surgeon. The depth perception for the user is limited. Since the user guides the endoscope with one hand, they also only have one hand free to hold surgical instruments.

SUMMARY

It is an object of the disclosure to provide a surgical microscope, in which the observation of capillaries and blood vessels in the upper mucosa and the underlying tissue is improved.

This object is achieved by an apparatus and a method as disclosed herein. Further, advantageous developments of the disclosure are described.

According to an aspect of the disclosure, a surgical microscope for visualizing a tissue region comprises an illumination device having a light source and an illumination beam path for illuminating an object region with an object plane, and an observation device having an observation beam path for imaging the object region with the object plane into an observation plane.

The surgical microscope includes a first polarizer, which can be coupled into the illumination beam path and is configured to polarize the illumination light in a first orientation, and a second polarizer, which can be coupled into the observation beam path and which has a second orientation at an angle between 80° and 100° relative to the first orientation. The polarization is linear.

In a first mode, the light source emits illumination light in a first wavelength range between 430 nanometer [nm] and 570 nm, typically between 450 nm to 550 nm, wherein, in the first mode, the first polarizer is coupled into the illumination beam path, and the second polarizer is coupled into the observation beam path.

The illumination of the object region with green and blue illumination light and coupling the first polarizer into the illumination beam path and coupling the second polarizer into the observation beam path take place at the same time.

The first mode, which in this application is also referred to as multispectral mode, permits the observer particularly good and largely reflection-free visualization of capillaries and blood vessels in the upper mucosa and the underlying tissue.

Blue wavelengths, for example between 420 nm and 490 nm or between 450 nm and 490 nm, and green wavelengths, for example between 490 nm and 550 nm or between 490 nm and 570 nm, have a penetration depth in mucosa tissue that is greatly reduced as compared to the color red. For example, Bashkatov et al., "Optical properties of human stomach mucosa in the spectral range from 400 to 2000 nm: Prognosis for gastroenterology," Medical Laser Application 22 (2007), 95-104 states that the penetration depth into the mucosa at wavelengths <570 nm is less than 800 micrometer [μm] and at wavelengths >570 nm is less than 1000 to 1800 μm. Removing the red wavelength from the illumination spectrum, for example between 570 nm to 750 nm, and illuminating with blue and green illumination light permits the representation of surface layers.

In addition, hemoglobin absorption in the green and blue wavelength ranges is significantly larger than in the red wavelength above 570 nm, as a result of which a dark-light contrast between blood-filled vessels and surrounding tissue is obtained.

The illumination of the object region or of the tissue region is effected by polarized light. Scattering in the tissue region results in depolarization of the reflected light. In the tissue of the mucosa, the polarized light is scattered at birefringent structures. Multiple scattering in the tissue at birefringent structures with different orientations results in a random distribution of the resulting polarization directions and consequently in depolarization of the light. Such multiple scattering at birefringent structures with different orientations occurs in particular in penetration depths of 300 μm and more. Therefore, substantially only back-scattered light coming from penetration depths of 300 μm has components with a polarization direction that is perpendicular to the original polarization direction. Light having a wavelength <570 nm and a polarization direction which is polarized substantially orthogonally with respect to polarized incident light therefore stems substantially from depths in the region between 300 μm and 800 μm. The detection of light in the wavelength range 430 nm to 570 nm, in particular between 450 nm and 550 nm, which is polarized substantially orthogonally with respect to polarized incident light, therefore does not only reduce reflections but also limits the obtained image information to a region between 300 μm and 800 μm of tissue located under the skin surface. The observer consequently obtains specific information relating to the course of blood vessels in the papillary dermis. This is achieved in particular when, in the first mode, the intensity of the illumination light in the wavelength range between 430 nm to 570 nm, in particular between 450 and 550 nm, is larger than in the remaining wavelength ranges by at least a factor 5, typically by at least a factor 10. Typically, in the first mode, the light source emits illumination light only in a first wavelength range between 430 nm and 570 nm, in particular between 450 nm and 550 nm.

The first polarizer in the illumination beam path and the second polarizer in the observation beam path do not affect the visualization of the capillaries and blood vessels of the tissue region as such but significantly enhance the effect brought about by the illumination of the mucosa tissue with the blue and green light.

The cross polarization, i.e., the orientation of the second polarizer relative to an orientation of the first polarizer in an orthogonal arrangement, additionally advantageously has the effect of effectively reducing reflections due to the liquid film on the mucosa. The orientations of the two polarizers do not necessarily have to form an angle of 90°. Typically, angle settings between 80° and 100° can also permit good visualization.

The combination of these effects thus results in good visualization and significantly improved contrast of the capillaries and blood vessels in the mucosa surface and in the underlying tissue. In principle, the aim of using the polarization filters is to only detect light that has already been scattered in the tissue and is not reflected directly back by the surface. This brings about the selective visualization of the tissue layer below the reflective mucosa surface in a region that is limited by the penetration depth of the blue and green light.

The clearly visible region, in which the tissue located under the mucosa is observable, can be, for example, 0.3 millimeter [mm].

An observer can observe this effect directly through the eyepiece. Additional digital image processing, for example the recording of the tissue region using a camera, digital analysis, and image processing of the recordings, and the superposition of digitally prepared image structures into the observation beam path are not necessary. The surgeon can observe the enhanced contrast directly through the eyepiece. An additional monitor and camera are not necessary. The surgical microscope can thus advantageously be embodied to be compact and cost-effective.

Surgical microscopes are generally stereoscopic. Direct stereoscopic image observation offers improved depth perception to the observer.

The observer or surgeon can work directly using the surgical microscope because the function of the multispectral mode is integrated directly in the surgical microscope. Switching to an additional endoscope is not necessary. The observer can advantageously work with both hands in situ. Neither is it necessary to use a hand to guide and control an endoscope.

According to an aspect of the disclosure, the light source, in a second mode, emits white illumination light, wherein the first polarizer is coupled out of the illumination beam path and the second polarizer is coupled out of the observation beam path.

In this second mode, the tissue region is illuminated with white light. The observer can observe the tissue region in normal view without specific structures, capillaries or blood vessels being particularly highlighted.

According to another aspect of the disclosure, the first orientation of the first polarizer and the second orientation of the second polarizer are orthogonal relative to one another.

In an orthogonal orientation, i.e., in a position of exactly 90°, the coupling of polarized illumination light into the observation beam path is blocked. Typically, only the light scattered by the mucosa and the underlying tissue region is observable and thus permits selective visualization of the region. The observable images exhibit good contrast. The blood vessels and capillaries are clearly visible.

According to an aspect of the disclosure, the light source is configured in the form of a light-emitting diode light source and has at least three individual light sources, wherein a first individual light source is configured to emit illumination light in a red wavelength range at least between 600 nm and 640 nm, a second individual light source is configured to emit illumination light in a green wavelength range at least between 500 nm and 570 nm, and a third individual light source is configured to emit illumination light in a blue wavelength range at least between 430 nm and 480 nm.

With a light-emitting diode light source having individual light sources, a desired wavelength range can be set by switching the individual light sources on or off. Filters can typically be dispensed with. The light source can be embodied to be more compact and cost-effective.

According to an aspect of the disclosure, the light-emitting diode light source emits, in the first mode, only illumination light from the second individual light source and the third individual light source, and emits, in the second mode, illumination light from the first individual light source, the second individual light source and the third individual light source.

A desired wavelength range can be set by switching the individual light sources on or off. It is possible to embody the control function more simply.

According to an aspect of the disclosure, the light source is configured in the form of a white light source which emits illumination light in a wavelength range between at least 450 nm and 620 nm, wherein, in the first mode, a red filter is coupled into the illumination beam path which effects attenuation of greater than 90%, typically larger than 95%, for wavelengths larger than 620 nm, typically larger than 600 nm, more typically larger than 570 nm.

In an exemplary embodiment, the light source is configured as a white light source. A white light source can be formed for example by a halogen or xenon light source. By using a red filter to block the red wavelength range, the object region is advantageously illuminated with a wavelength range including the blue and green wavelength ranges.

According to an aspect of the disclosure, switching between the first mode and the second mode is effected by an individual switching element.

When switching from the first mode into the second mode, at least three actions must be performed. Controlling the light source, coupling the first polarizer into or out of the illumination beam path, and coupling the second polarizer into or out of the observation beam path. This is typically effected by way of an individual switching element so that a user can bring about the switch quickly and easily.

The user can thus switch between the second mode, i.e., white light illumination, and the first mode, i.e., multispectral mode, with a single interaction without interrupting the workflow.

According to an aspect of the disclosure, the switching element is embodied in the form of an element of a graphical user interface or as a switch in a foot control panel.

The integration into a graphical user interface or operator interface is cost-effective because no additional physical switch and associated wiring need to be set up. The exemplary embodiment in the form of a physical switch in a foot control panel allows the user to switch without distraction. That means the user can work with both hands at the operating location without interrupting the workflow and does not need to turn the gaze away from the eyepieces of the surgical microscope.

According to an aspect of the disclosure, the object plane is recordable by at least one camera arranged in the observation beam path.

Recording the object region with a camera permits producing a record of and documenting the surgical procedure. In addition, the image of the operating location is displayable on a screen.

The surgical microscope can be a conventional optical stereo surgical microscope having a main objective, a magnification optical unit and eyepieces, or it can be a purely digital surgical microscope in which the object plane is recorded by one or more cameras, the image of which is displayed on a screen. The surgical microscope can also form a hybrid system, a mixture of a conventional surgical microscope and a digital surgical microscope.

One or more cameras can be arranged in addition to the eyepieces in the surgical microscope. Furthermore, a beam splitter, having a camera arranged on the second side thereof, can be arranged in the observation beam path. In an alternative exemplary embodiment, the eyepieces can also be replaced by cameras.

In the method according to an aspect of the disclosure for visualizing an object region as disclosed in one of the preceding aspects, the object region with an object plane is illuminated, in a first mode, with illumination light, which is linearly polarized in a first orientation, in a first wavelength range between 430 nm and 570 nm, typically between 450 nm and 550 nm. The illuminated object region is observed using an observation apparatus with an observation beam path for imaging the object plane into an observation plane. A second polarizer having a second orientation at an angle between 80° and 100° relative to the first orientation is coupled into the observation beam path.

It is possible with the method according to the aspect of the disclosure to limit the visualization of the object region in the first mode to the visualization of an object region with a depth in the range of 300 to 800 nm. Here, a synergy effect exists between the selected wavelength range and the use of the polarizers in as far as the selected wavelength range ensures that the penetration depth of the light is less than 800 μm, while the polarization ensures that the light detected as part of the visualization substantially comes from a penetration depth of 300 μm and more. It is advantageous here when, in the first mode, the intensity of the illumination light in the wavelength range between 430 nm to 570 nm, in particular between 450 and 550 nm, is larger than in the remaining wavelength ranges by at least a factor 5, typically by at least a factor 10. It is particularly advantageous if, in the first mode, the light source emits illumination light only in a first wavelength range between 430 nm and 570 nm, in particular between 450 nm to 550 nm.

According to a further aspect of the disclosure, provision is made of a surgical microscope for visualizing a tissue region. The surgical microscope includes:

an illumination device having a light source and an illumination beam path for illuminating an object region with an object plane, an observation device having an observation beam path for imaging the object region with the object plane into an observation plane, a first polarizer, which can be coupled into the illumination beam path and is configured for polarizing the illumination light in a first orientation, a second polarizer, which can be coupled into the observation beam path and has a second orientation at an angle between 80° and 100° relative to the first orientation, wherein in a first mode, the light source emits illumination light within the absorption spectrum of hemoglobin and with wavelengths in the wavelength region below 570 nm, and in the first mode, the first polarizer is coupled into the illumination beam path, and the second polarizer is coupled into the observation beam path. The intensity of the illumination light in the wavelength range above 570 nm, in the first mode, is here lower than in the remaining wavelength ranges typically by at least a factor 5, in particular by at least a factor 10.

According to yet another aspect of the disclosure, a method for visualizing an object region is disclosed, wherein the object region with an object plane is illuminated in a first mode using an illumination device, having a light source and an illumination beam path, and a polarizer, which can be coupled into the illumination beam path, with illumination light, polarized in a first orientation, in a first wavelength region within the absorption spectrum of hemoglobin and below 570 nm, and the illuminated object region is observed using an observation device having an observation beam path for imaging the object plane into an observation plane, wherein a second polarizer having a second orientation at an angle between 80° and 100° relative to the first orientation is coupled into the observation beam path. The intensity of the illumination light in the wavelength range above 570 nm, in the first mode, is here lower than in the remaining wavelength ranges typically by at least a factor 5, in particular by at least a factor 10.

BRIEF DESCRIPTION OF THE DRAWINGS

The disclosure will now be described with reference to the drawings wherein.

DESCRIPTION OF EXEMPLARY EMBODIMENTS

The present disclosure will be explained below by way of the example of a surgical microscope. With respect to FIGS. 1 and 2, the basic setup of the surgical microscope 2 is therefore described.

Figure 1:
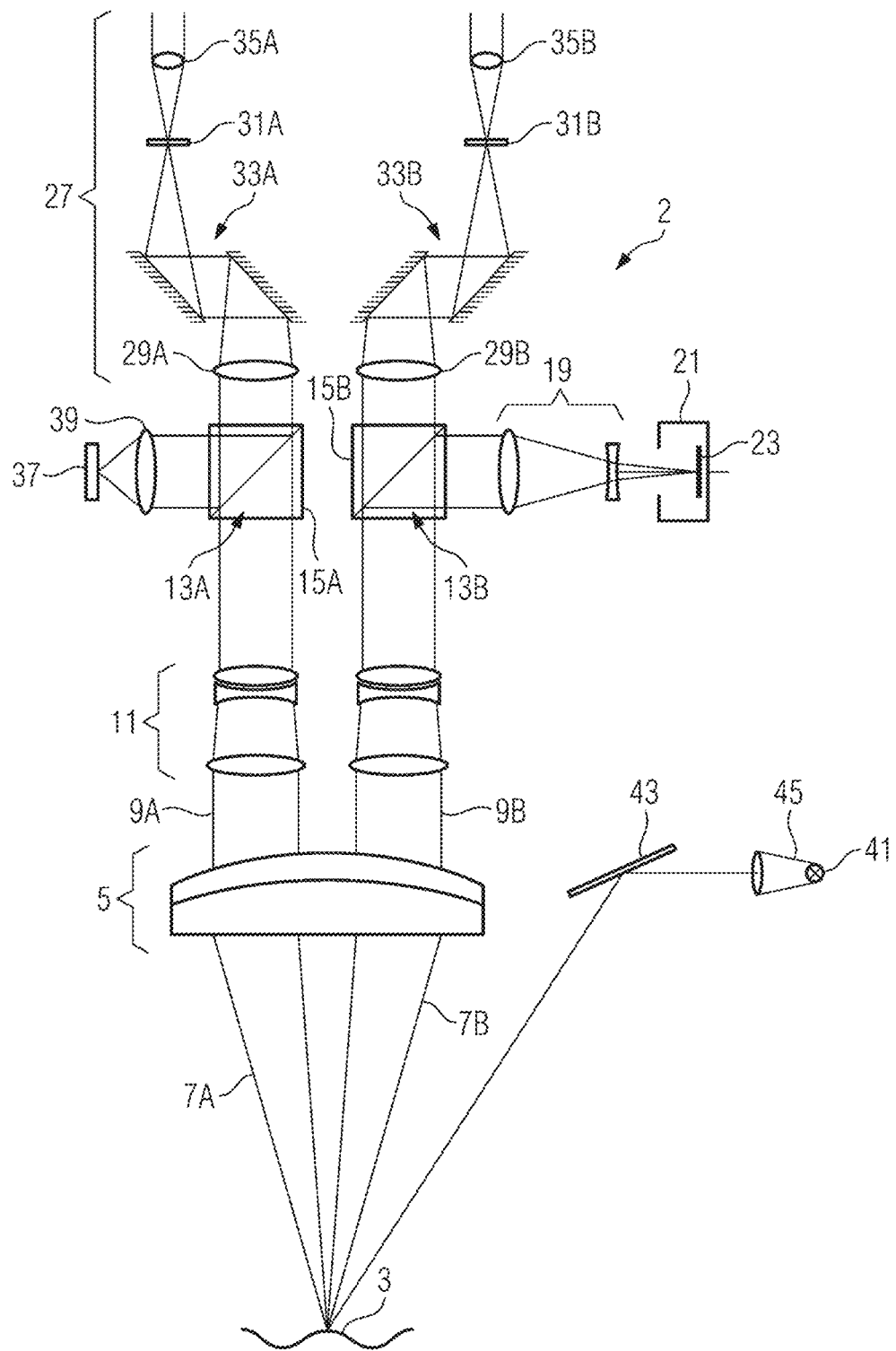
FIG. 1 shows a schematic illustration of typical optical components of a surgical microscope.

The surgical microscope 2 shown in FIG. 1 includes, as essential optical components, an objective 5 that is to face an object field 3, the objective, in particular, can be embodied as an achromatic or apochromatic objective. In the present exemplary embodiment, the objective 5 contains two partial lenses that are cemented to one another and form an achromatic objective. In the case of an apochromatic objective, at least three partial lenses would be present. The object field 3 is arranged in the focal plane of the objective 5 such that an observation object located in the object field 3 is imaged at infinity by the objective 5. Expressed differently, a divergent beam 7 emanating from the object field 3 is converted into a parallel beam 9 during its passage through the objective 5.

A magnification changer 11 is arranged on the observer side of the objective 5, which magnification changer can be embodied either as a zoom system for changing the magnification factor in a continuously variable manner as in the illustrated exemplary embodiment, or as what is known as a Galilean changer for changing the magnification factor in a stepwise manner. In a zoom system, constructed by way of example from a lens combination having three lenses, the two object-side lenses can be displaced in order to vary the magnification factor. However, the zoom system also can have more than three lenses, for example four or more lenses, in which case the outer lenses then can also be arranged in a fixed manner. In a Galilean changer, by contrast, there is a plurality of fixed lens combinations which represent different magnification factors, and which can be introduced into the beam path alternately. Both a zoom system and a Galilean changer convert an object-side parallel beam into an observer-side parallel beam having a different beam diameter.

In the present exemplary embodiment, the magnification changer 11 already is part of the binocular beam path of the surgical microscope 2, i.e., it has a dedicated lens combination for each stereoscopic partial beam path 9A, 9B of the surgical microscope 2. However, it is also possible in principle to use a "large magnification changer," i.e., a magnification changer in which both stereoscopic partial beam paths pass through each lens.

A magnification factor is set, in the present exemplary embodiment, with the magnification changer 11 by way of a motor-driven actuator which, together with the magnification changer 11, is part of a magnification changing unit for setting the magnification factor.

The magnification changer 11 is adjoined on the observer side by an optical interface arrangement 13A, 13B, by which external appliances can be connected to the surgical microscope 2 and which includes beam splitter prisms 15A, 15B in the present exemplary embodiment. However, in principle, use can also be made of other types of beam splitters, for example partly transmissive mirrors. In the present exemplary embodiment, the optical interfaces 13A, 13B serve to couple a beam out of the beam path of the surgical microscope 2 (beam splitter prism 15B) and to couple a beam into the beam path of the surgical microscope 2 (beam splitter prism 15A).

In the present exemplary embodiment, the beam splitter prism 15A in the partial beam path 9A serves to mirror information or data for an observer into the partial beam path 9A of the surgical microscope 1 with the aid of a display 37, for example a digital mirror device (DMD) or an LCD display, and an associated optical unit 39 by the beam splitter prism 15A. A camera adapter 19 with a camera 21 fastened thereto, the camera being equipped with an electronic image sensor 23, for example with a CCD sensor or a CMOS sensor, is arranged at the interface 13B in the other partial beam path 9B. It is possible to record a digital image with the camera 21 and, in particular, a digital image of the object field 3.

The interfaces 13A, 13B are adjoined on the observer side by a binocular tube 27. The latter has two tube objectives 29A, 29B, which focus the respective parallel beam 9A, 9B onto intermediate image planes 31A, 31B, i.e., image the object field 3 onto the respective intermediate image planes 31A, 31B. The intermediate images situated in the intermediate image planes 31A, 31B are finally imaged at infinity in turn by eyepiece lenses 35A, 35B, such that an observer can observe the intermediate image with a relaxed eye. Moreover, an increase in the distance between the two partial beams 9A, 9B is effectuated in the binocular tube with a mirror system or by prisms 33A, 33B to adapt the distance to the interocular distance of the observer. In addition, image erection is carried out by the mirror system or the prisms 33A, 33B.

The surgical microscope 2 moreover is equipped with an illumination device, by which the object field 3 can be illuminated with illumination light. To this end, the illumination device in the present exemplary embodiment has a white light source 41, for example a halogen lamp or a gas discharge lamp. The light emanating from the white light source 41 is directed in the direction of the object field 3 via a deflection mirror 43 or a deflection prism to illuminate the field. Furthermore, an illumination optical unit 45 is present in the illumination device, the illumination optical unit ensuring uniform illumination of the entire observed object field 3.

Reference is made to the fact that the illumination beam path illustrated in FIG. 1 is highly schematic and does not necessarily reproduce the actual course of the illumination beam path. In principle, the illumination beam path can be embodied as what is known as oblique illumination, which comes closest to the schematic illustration in FIG. 1. In such oblique illumination, the beam path extends at a relatively large angle (6° or more) with respect to the optical axis of the objective 5 and, as illustrated in FIG. 1, may extend completely outside the objective. Alternatively, however, there is also the possibility of allowing the illumination beam path of the oblique illumination to extend through a marginal region of the objective 5. A further option for the configuration of the illumination beam path is what is known as 0° illumination, in which the illumination beam path extends through the objective 5 and is coupled into the objective 5 between the two partial beam paths 9A, 9B, along the optical axis of the objective 5 in the direction of the object field 3. Finally, it is also possible to embody the illumination beam path as what is known as coaxial illumination, in which a first illumination partial beam path and a second illumination partial beam path are present. The partial beam paths of the illumination beam path are coupled into the surgical microscope in a manner parallel to the optical axes of the observation partial beam paths 9A, 9B by way of one or more beam splitters, such that the illumination extends coaxially in relation to the two observation partial beam paths.

In the exemplary embodiment of the surgical microscope 2 shown in FIG. 1, the objective 5 consists only of an achromatic lens. However, use can also be made of an objective lens system made of a plurality of lenses, in particular what is known as a varioscope objective, by which it is possible to vary the working distance of the surgical microscope 2, i.e., the distance between the object-side focal plane and the vertex of the first object-side lens surface of the objective 5, also referred to as front focal distance. The object field 3 arranged in the focal plane is imaged at infinity by the varioscope objective 50, too, and so a parallel beam is present on the observer side.

Figure 2:
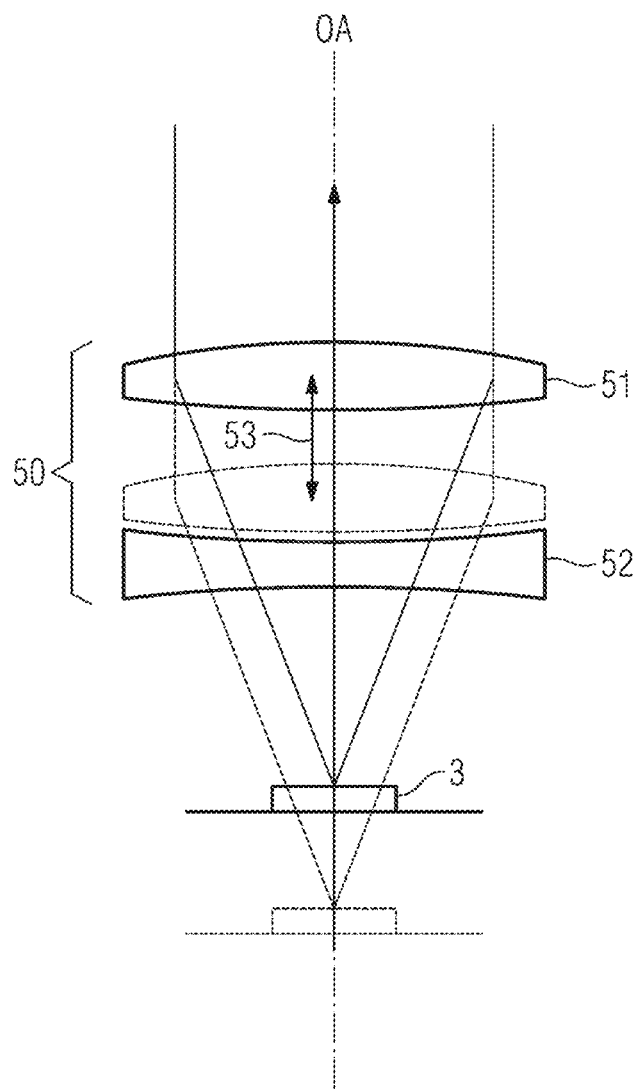
FIG. 2 shows a schematic illustration of a varioscope objective.

One exemplary embodiment of a varioscope objective is illustrated schematically in FIG. 2. The varioscope objective 50 includes a positive member 51, i.e., an optical element having positive refractive power, which is schematically illustrated as a convex lens in FIG. 2. Moreover, the varioscope objective 50 includes a negative member 52, i.e., an optical element having negative refractive power, which is schematically illustrated as a concave lens in FIG. 2. The negative member 52 is situated between the positive member 51 and the object field 3. In the illustrated varioscope objective 50, the negative member 52 has a fixed arrangement, whereas, as indicated by the double-headed arrow 53, the positive member 51 is arranged to be displaceable along the optical axis OA. When the positive member 51 is displaced into the position illustrated by dashed lines in FIG. 2, the back focal length increases, and so there is a change in the working distance of the surgical microscope 2 from the object field 3.

Even though the positive member 51 has a displaceable configuration in FIG. 2, it is also possible, in principle, to arrange the negative member 52 to be movable along the optical axis OA instead of the positive member 51. However, the negative member 52 often forms the last lens of the varifocal objective 50. A stationary negative member 52 therefore offers the advantage of making it easier to seal the interior of the surgical microscope 2 from external influences. Furthermore, it is noted that, even though the positive member 51 and the negative member 52 in FIG. 2 are only illustrated as individual lenses, each of these members may also be realized in the form of a lens group or a cemented element instead of in the form of an individual lens, for example to embody the varioscope objective to be achromatic or apochromatic.

Figure 3:
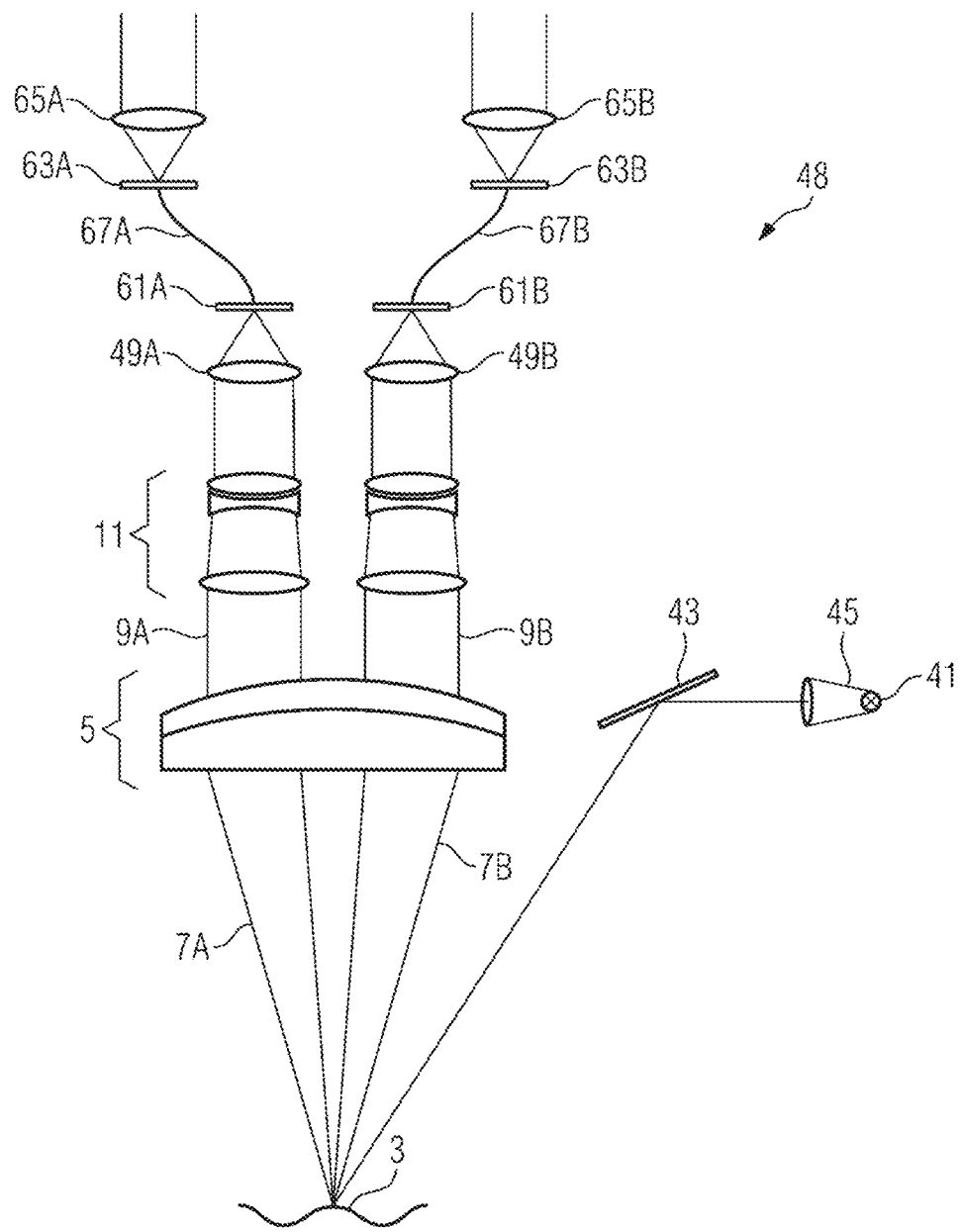
FIG. 3 shows the surgical microscope from FIG. 1 configured as a digital surgical microscope.

FIG. 3 shows a schematic illustration of an example of a digital surgical microscope 48. In this surgical microscope, the main objective 5, the magnification changer 11 and the illumination system 41, 43, 45 do not differ from the surgical microscope 2 with the optical view that is illustrated in FIG. 1. The difference lies in the fact that the surgical microscope 48 shown in FIG. 3 does not include an optical binocular tube. Instead of the tube objectives 29A, 29B shown in FIG. 1, the surgical microscope 48 depicted in FIG. 3 includes focusing lenses 49A, 49B, by which the binocular observation beam paths 9A, 9B are imaged onto digital image sensors 61A, 61B. Here, the digital image sensors 61A, 61B can be, e.g., charge-coupled device (CCD) sensors or complementary metal-oxide semiconductor (CMOS) sensors. The images recorded by the image sensors 61A, 61B are transmitted digitally to digital displays 63A, 63B, which may be embodied as light-emitting diodes (LED) displays, as liquid-crystal display (LCD) displays, or as displays based on organic light-emitting diodes (OLEDs). Like in the present exemplary embodiment, eyepiece lenses 65A, 65B can be assigned to the displays 63A, 63B, by which the images displayed on the displays 63A, 63B are imaged at infinity such that an observer can observe the images with relaxed eyes. The displays 63A, 63B and the eyepiece lenses 65A, 65B can be part of a digital binocular tube; however, they can also be part of a head-mounted display (HMD) such as, a pair of smartglasses.

Even though FIG. 3, like FIG. 1, only illustrates an achromatic lens 5 with a fixed focal length, the surgical microscope 48 shown in FIG. 3 may include an apochromatic objective or a varioscope objective instead of the achromatic lens 5, like the surgical microscope 2 illustrated in FIG. 1. Furthermore, FIG. 3 shows a transfer of the images recorded by the image sensors 61A, 61B to the displays 63A, 63B by cables 67A, 67B. However, instead of in a wired manner, the images can also be transferred wirelessly to the displays 63A, 63B, especially if the displays 63A, 63B are part of a head-mounted display.

Figure 4:
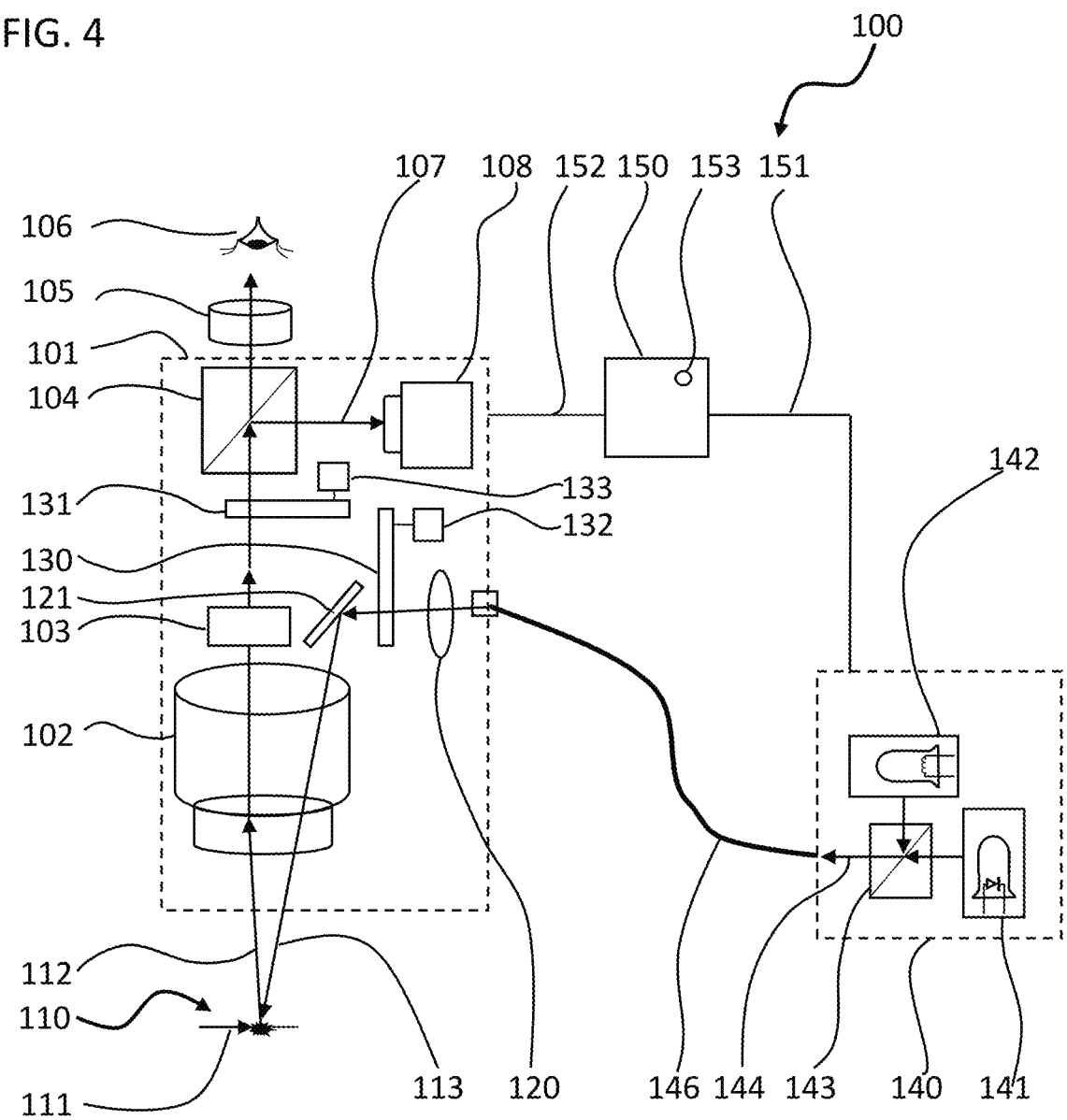
FIG. 4 shows a surgical microscope in a schematic illustration according to an exemplary embodiment of the disclosure.

FIG. 4 shows a surgical microscope in a schematic illustration according to an exemplary embodiment of the disclosure.

A surgical microscope system 100 includes a surgical microscope 101, a light source unit 140 and a control unit 150. The surgical microscope includes an observation device having an observation beam path 112 and an illumination device having an illumination beam path 113.

The observation device includes a main objective 102, a magnification changer 103, a first beam splitter 104, and an eyepiece 105, which are arranged along the observation beam path 112. An object region 110 with an object plane 111 can be observed by an observer, illustrated by a schematically illustrated eye 106, through the eyepiece 105.

The observation device is illustrated schematically. The observation beam path 112 is stereoscopic and includes two partial beam paths (not illustrated).

The first beam splitter 104, arranged in the observation beam path 112, couples out part of the observation light and images it, via the camera beam path 107, onto the sensor of a camera 108, with the result that the object region 110 with the object plane 111 is capturable by the camera 108. The camera 108 can have a stereoscopic embodiment.

The light source unit 140 includes a first light source 141 and a second light source 142. The first light source 141 is embodied in the form of a light-emitting diode light source and includes three individual light sources for the colors red, green, and blue. The light-emitting diode light source is also referred to as an RGB light source. The light source unit 140 is connected to the control unit 150 via a first line 151, with the result that each individual light source is separately actuable.

The illumination light emitted by the first light source 141 is guided via a second beam splitter 143 along an illumination-light beam path 144 and coupled into an optical waveguide 146, for example a fiber-optic cable. The illumination light of the second light source 142 is coupled into the illumination-light beam path 144 via the beam splitter 143. The second light source 142 can be formed for example by an individual light source emitting violet light.

The optical waveguide 146 is connected to the surgical microscope 101. The illumination light is guided along the illumination beam path 113 to the object region 110 with the object plane 111. An illumination optical unit 120 is arranged in the illumination beam path 113. The illumination beam path 113 is deflected via a deflection mirror 122 and guided through the main objective 102 to the object plane 111.

A first polarizer 130 is arranged in the illumination beam path 113 between the illumination optical unit 120 and the deflection mirror 121. The first polarizer 130 can be coupled into and out of the illumination beam path 113. To this end, the first polarizer 130 is movable by way of a first actuator 132. The first actuator 132 is connected to the controller 150.

A second polarizer 131 is arranged in the observation beam path 112 between the magnification changer 103 and the first beam splitter 104. The second polarizer 131 can be coupled into and out of the observation beam path 112. To this end, the second polarizer 131 is movable by way of a second actuator 133. The second actuator 133 is connected to the controller 150.

In a white light mode, the second made, the first polarizer 130 is coupled out of the illumination beam path 113 and the second polarizer 131 is coupled out of the observation beam path 112. The first light source 141 emits white illumination light. This is attained by way of all individual light sources, i.e., the red, green, and blue individual light sources, being switched on. In this second mode, a tissue region located in the object plane 111 is illuminated with white light. The observer can observe the tissue region in normal view without specific structures, capillaries or blood vessels being particularly highlighted.

The control unit 150 is connected to a switching element 153. Upon actuation of the switching element 153, the first mode, the multispectral mode, is activated by way of the control unit 150. To this end, the red individual light source of the first light source 141 is switched off, while the green and blue individual light sources remain switched on. At the same time, the first polarizer 130 is coupled into the illumination beam path by way of the first actuator 132, and the second polarizer 131 is coupled into the observation beam path by way of the second actuator 132. This multispectral mode thus results in good visualization and significantly improved contrast of the capillaries and blood vessels in the mucosa and in the underlying tissue.

The observer observes the image filtered by the second polarizer 131 directly through the eyepieces. The camera 108, which is optional, records a single channel or both channels of the stereoscopic image. No additional digital filtering is necessary to produce the contrast between tissue and blood vessel in the video signal.

Another actuation of the switching element 153 once again sets the white light mode. To this end, the red individual light source of the first light source 141 is switched on again. The first polarizer 130 is coupled out of the illumination beam path by way of the first actuator 133, and the second polarizer 131 is coupled out of the observation beam path by way of the second actuator 133. These procedures are performed at the same time. In an alternative aspect, they may also be performed successively in time.

The surgical microscope 101 can be a conventional optical stereo surgical microscope with eyepieces or may be embodied in the form of a purely digital surgical microscope only with cameras. The surgical microscope 101 can be embodied in the form of a hybrid system, a mixture of a conventional surgical microscope and a digital surgical microscope with the camera 108.

Figure 5:
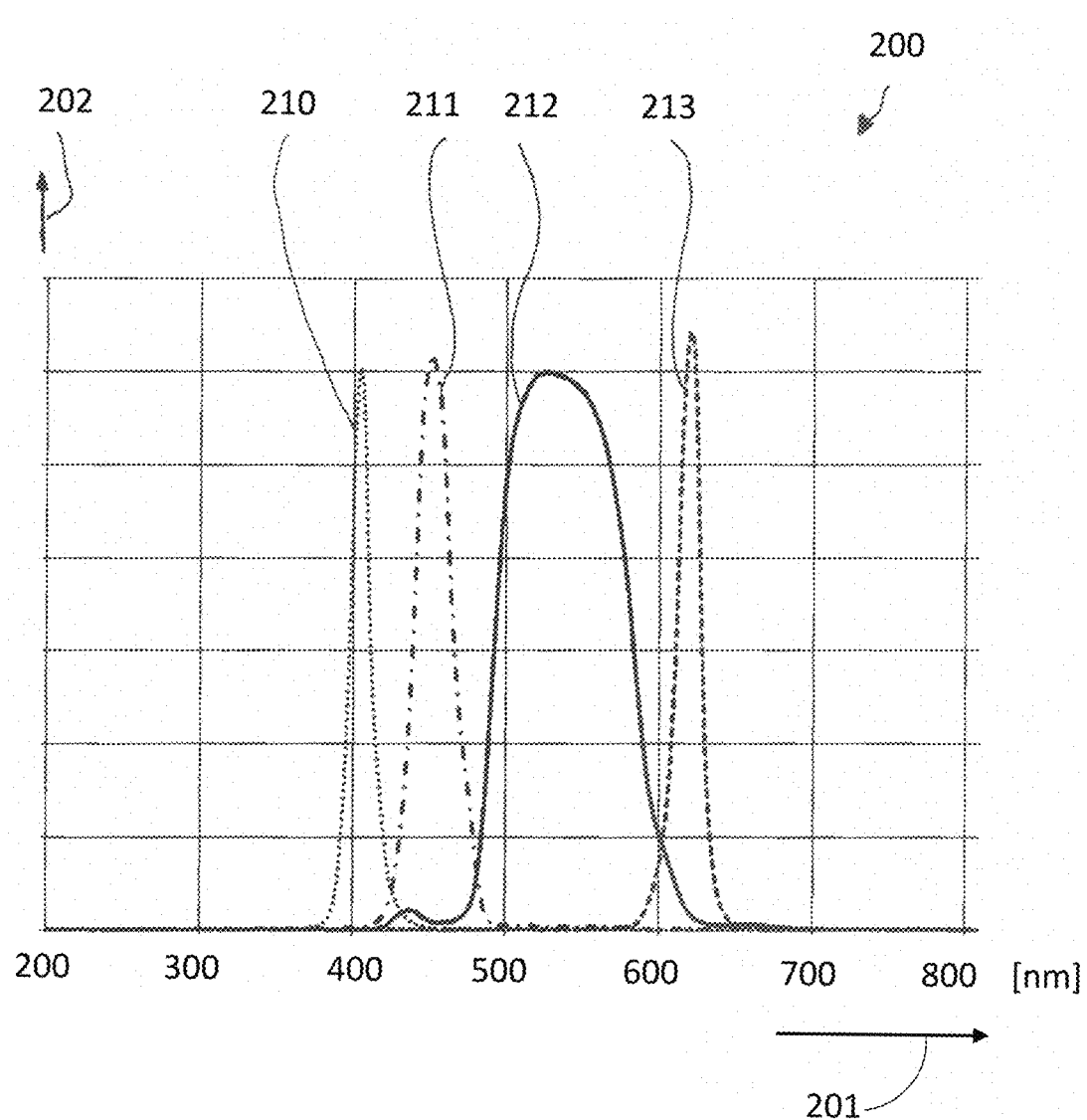
FIG. 5 shows a diagram illustrating a radiation pattern of the individual light sources of the first light source and of the second light source in accordance with FIG. 4.

FIG. 5 shows a diagram 200 illustrating an exemplary embodiment of a radiation pattern of the individual light sources of the first light source and of the second light source in accordance with FIG. 4.

An abscissa 201 indicates the wavelength range of the emitted light between 200 nm and 800 nm. An ordinate 202 indicates an intensity.

A first curve 210 shows the radiation pattern of the second light source 142 with respect to the exemplary embodiment according to FIG. 4.

A second curve 211 shows the radiation pattern of the blue individual light source of the first light source 141 with respect to the exemplary embodiment according to FIG. 4. The emitted light of the first blue individual light source is emitted in a wavelength range between 420 nm and 480 nm.

A third curve 212 shows the radiation pattern of the green individual light source of the first light source 141 with respect to the exemplary embodiment according to FIG. 4. The emitted light of the green individual light source is emitted in a wavelength range between 480 nm and 600 nm.

A fourth curve 213 shows the radiation pattern of the red individual light source of the first light source 141 with respect to the exemplary embodiment according to FIG. 4. The emitted light of the red individual light source is emitted in a wavelength range between 600 nm and 640 nm.

Figure 6:
FIG. 6 shows a tissue region illuminated with conventional white light illumination in the second mode.

FIG. 6 shows a tissue region illuminated with conventional white light illumination. The surgical microscope in accordance with FIG. 4 is set in a second mode.

Figure 7:
FIG. 7 shows the tissue region in accordance with FIG. 6, illuminated in the multispectral mode.

FIG. 7 shows the tissue region in accordance with FIG. 6, illuminated in the multispectral mode. The FIG. 7 shows the improved contrast between tissue and blood vessels in the multispectral mode.

In an alternative exemplary embodiment of the disclosure, the object region with the object plane is illuminated in the first mode using the light source 141 with illumination light in a wavelength range within the absorption spectrum of hemoglobin and below 570 nm. The intensity of the illumination light in the wavelength range above 570 nm is here lower than in the remaining wavelength ranges typically by at least a factor 5, in particular by at least a factor 10. In addition, the first polarizer 131 is introduced in the illumination beam path 113 with a first orientation, with the result that the illumination light is polarized with the first orientation. In addition, the second polarizer 131 is coupled into the observation beam path 112. The second polarizer 131 has a second orientation at an angle between 80° and 100° relative to the first orientation of the first polarizer.

Owing to the illumination light having wavelengths <570 nm, the penetration depth of the illumination light in mucosal tissue is less than 800 µm. Removing the red wavelengths from the illumination spectrum, i.e., wavelengths >570 nm, and illuminating with blue and green illumination light, i.e., with wavelengths <570 nm, limits the representation substantially to surface layers with a depth of less than 800 µm. In addition, hemoglobin absorption in the green and blue wavelength ranges is significantly greater than in the red wavelength above 570 nm, as a result of which a dark-light contrast between blood-filled vessels and surrounding tissue is obtained. The polarizers additionally have the effect that the light that is scattered back by the mucosal tissue comes from penetration depths of 300 µm and more, with the result that the image information obtained with the observation beam path is limited to a range between 300 and 800 µm of tissue located under the skin surface.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

2 Surgical microscope
3 Object region
5 Objective
7 Divergent beam
9 Beam
9A, 9B Stereoscopic partial beam path
11 Magnification changer
13A, 13B Interface arrangement
15A, 15B Beam splitter prism
19 Camera adapter
21 Camera
23 Image sensor
27 Binocular tube
29A, 29B Tube objective
31A, 31B Intermediate image plane
33A, 33B Prism
35A, 35B Eyepiece lens
37 Display
39 Optical unit
41 White light source
43 Deflection mirror
45 Illumination optical unit
48 Digital surgical microscope
49A, 49B Focusing lens
50 Varifocal objective
51 Positive member
52 Negative member
53 Displacement path
100 Surgical microscope system
101 Surgical microscope
102 Main objective
103 Magnification changer
104 First beam splitter
105 Eyepiece
106 Eye of an observer
107 Camera beam path
108 Camera
110 Object region
111 Object plane
112 Observation beam path
113 Illumination beam path
120 Illumination optical unit
121 Deflection mirror
130 First polarizer
131 Second polarizer
132 First actuator
133 Second actuator
140 Light source unit
141 First light source
142 Second light source
143 Second beam splitter
144 Illumination-light beam path
146 Optical waveguide
150 Control unit
151 First line
152 Second line
153 Switching element
200 Diagram
201 Abscissa
202 Ordinate
210 First curve
211 Second curve
212 Third curve
213 Fourth curve

What is claimed is:

1. A method for visualizing an object region of an object in situ with a surgical microscope, the method comprising:
limiting a visualization of a tissue in the object region of the object in situ in a first mode to a penetration depth in a range between 300 µm to 800 µm by execution of:
coupling a first polarizer into an illumination beam path;
orienting the first polarizer in a first direction to polarize an illumination light emitted by a light source including individual light sources emitting light in different wavelength ranges;
illuminating the object region in an object plane with the illumination light in the first mode, wherein the illumination light is polarized in a first orientation and has a first wavelength range between 430 nm and 570 nm emitted by one or more of the individual light sources, and wherein wavelengths in a second wavelength range between 570 nm and 750 nm are removed from a spectrum of the illumination light by switching one or more of the individual light sources emitting in the wavelength range between 570 nm and 750 nm off;

coupling a second polarizer into an observation beam path;

orienting the second polarizer to have a second orientation at an angle between 80° and 100° relative to the first orientation; and observing the illuminated object region with an observation device through the observation beam path, where illuminating the object region and observing the illuminated object region both take place from a same side of the object.

2. The method as claimed in claim 1, wherein, in the first mode, an intensity of the illumination light in the first wavelength range between 430 nm to 570 nm is larger than the intensity in the remaining wavelength ranges by at least a factor of 5.

3. The method as claimed in claim 2, wherein, in the first mode, the light source emits the illumination light only in the first wavelength range between 430 nm and 570 nm.

4. A method for visualizing an object region of an object in situ, the method comprising:

providing an illumination device including a light source emitting illumination light including individual light sources emitting light in different wavelength ranges to propagate along an illumination beam path and to illuminate an object region including an object plane and a first polarizer configured to be coupled into the illumination beam path;

limiting a visualization of a tissue in the object region of the object in situ in a first mode to a penetration depth in a range between 300 µm to 800 µm by execution of:

coupling the first polarizer into the illumination beam path and orienting the first polarizer in a first orientation to polarize the illumination light;

illuminating, in a first mode, the object region in the object plane with the illumination light polarized in the first orientation, wherein a wavelength of the illumination light is in a first wavelength region within an absorption spectrum of hemoglobin and below 570 nm emitted by one or more of the individual light sources, and wherein wavelengths in a range between 570 nm and 750 nm are removed from a spectrum of the illumination light by switching one or more of the individual light sources emitting in the wavelength range between 570 nm and 750 nm off;

coupling a second polarizer having a second orientation at an angle between 80° and 100° relative to the first orientation into an observation beam path of an observation apparatus;

imaging the object region into an observation plane along the observation beam path; and observing the object region imaged into the observation plane with the observation apparatus, where illuminating the object region and observing the illuminated object region both take place from a same side of the object.

5. The method as claimed in claim 4, wherein, in the first mode, an intensity of the illumination light in the wavelength range above 570 nm is lower than the intensity in the remaining wavelength ranges by at least a factor of 5.

* * * * *